United States Patent
Kato et al.

(10) Patent No.: US 7,666,141 B2
(45) Date of Patent: Feb. 23, 2010

(54) ULTRASONIC DIAGNOSTIC APPARATUS

(75) Inventors: Makoto Kato, Kanagawa (JP); Yoshinao Tannaka, Kanagawa (JP)

(73) Assignee: Panasonic Corporation, Kadoma (JP)

( * ) Notice: Subject to any disclaimer, the term of this patent is extended or adjusted under 35 U.S.C. 154(b) by 356 days.

(21) Appl. No.: 11/577,075

(22) PCT Filed: Oct. 18, 2005

(86) PCT No.: PCT/JP2005/019089
§ 371 (c)(1),
(2), (4) Date: Apr. 11, 2007

(87) PCT Pub. No.: WO2006/043529
PCT Pub. Date: Apr. 27, 2006

(65) Prior Publication Data
US 2009/0024032 A1    Jan. 22, 2009

(30) Foreign Application Priority Data
Oct. 19, 2004    (JP)    ............................. 2004-304674

(51) Int. Cl.
*A61B 8/00*    (2006.01)
(52) U.S. Cl. .................................... 600/443
(58) Field of Classification Search ................. 600/440, 600/425, 437–444, 449, 463, 466; 382/167, 382/579, 596.645, 573; 348/43; 378/4; 345/426, 424
See application file for complete search history.

(56) References Cited

U.S. PATENT DOCUMENTS 5,840,028 A    11/1998    Chubachi et al.

(Continued)

FOREIGN PATENT DOCUMENTS

JP    10-005226    1/1998

(Continued)

OTHER PUBLICATIONS

Transactions on Ultrasound, Ferroelectrics and Frequency Control, ("Real-Time Measurements of Local Myocardium Motion and Arterial Wall Thickening" (1999)) by Kanai et al.*

(Continued)

*Primary Examiner*—Eric F Winakur
*Assistant Examiner*—Lawrence N Laryea
(74) *Attorney, Agent, or Firm*—Renner, Otto, Boisselle & Sklar, LLP

(57) ABSTRACT

An ultrasonic diagnostic apparatus includes: a transmitting section for driving a probe transmitting an ultrasonic wave to a subject; a receiving section for amplifying a reflected echo, produced by getting the ultrasonic wave reflected by a tissue and received at the probe, to generate a received signal; an image processing section for generating a tomographic image of the subject based on the signal; a region setting section for setting an arbitrary range of the tomographic image as a region of interest; a motion information gathering section for getting the motion information of the subject at measuring points on the subject based on the signal; a property value calculating section for calculating the property values of target tissues of the subject, specified by the measuring points, by reference to the motion information; and a distribution plotting section, which gets the property measured values and plots a frequency distribution of the property values based on the property values of the target tissues located within the region of interest set by the setting section.

13 Claims, 5 Drawing Sheets

U.S. PATENT DOCUMENTS

| | | | |
|---|---|---|---|
| 6,132,373 | A | 10/2000 | Ito et al. |
| 6,508,768 | B1 * | 1/2003 | Hall et al. .................. 600/443 |
| 2004/0260180 | A1 * | 12/2004 | Kanai et al. ................. 600/449 |

FOREIGN PATENT DOCUMENTS

| | | |
|---|---|---|
| JP | 11-318896 | 11/1999 |
| JP | 2000-271117 | 10/2000 |

OTHER PUBLICATIONS

Japanese Journal of Applied Physics ("Accuracy Evolution in the Measurement of a small Change in the Thickness of Arterial Arterial Walls and the Measurement of Elasticity of Human Carotid Artery(1998)") by Kanai et al.* http://en.wikipedia.org/wiki/Computer-aided_design.* http://en.wikipedia.org/wiki/Matlab : http://www.mathworks.com/.*

International Search Report for corresponding Application No. PCT/JP2005/019089 mailed Jan. 24, 2006.

Hiroshi Kanai et al.; "Elasticity Imaging of Atheroma with Transcutaneous Ultrasound Preliminary Study"; Circulation, vol. 107, 2003, pp. 3018-3021. (Cited in [0010], p. 5 of the description).

Hiroshi Kanai et al.; "Imaging of Elasticity Distribution in Arterial Wall by Transcutaneous Ultrasound and Electronic Staining;" Clinial Pathology, vol. 51; 2003; pp. 805-812.

Hideyuki Hasegawa et al.; "Ultrasonic Measurement of Regional Elasticity for Tissue Characterization of Arterial Wall;" The $3^{rd}$ International Symposium on Future Medical Engineering based on Bio-Nanotechnology; 2003; pp. 68-71.

B.H. Ong et al.; "Clinical Demonstration of Functional Wave Front of the Intramyocardial Ischemic Region in Patients with Coronary Stenosis;" IEEE Ultrasonics Symposium Proceedings; 2003; pp. 1843-1846.

Form PCT/ISA/237 and a concise explanation.

* cited by examiner

FIG.5
(a)
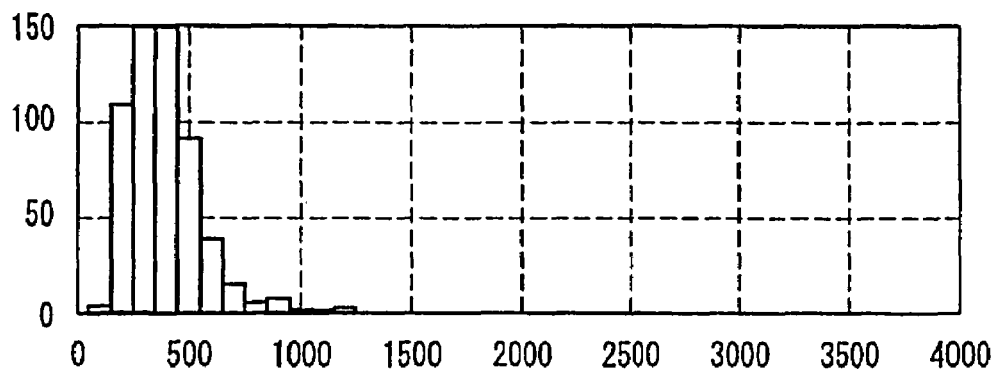
(b)
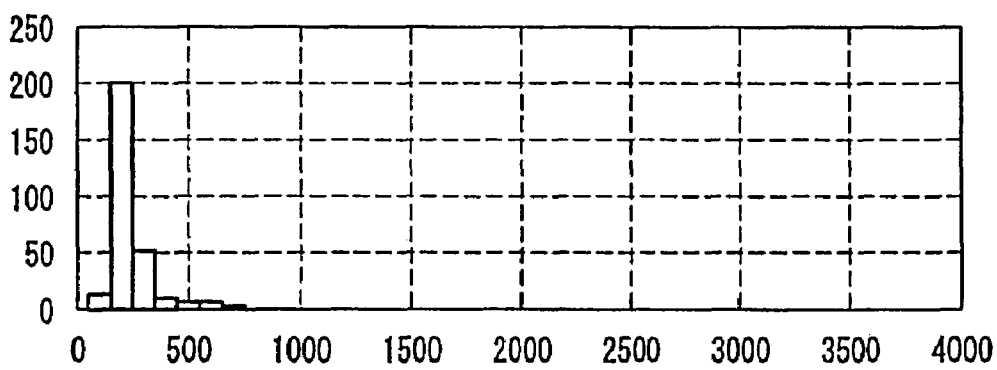
(c)
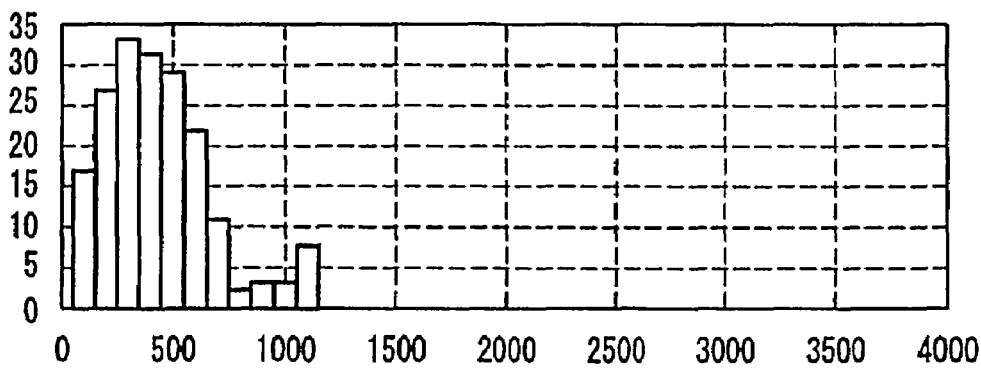

ULTRASONIC DIAGNOSTIC APPARATUS

TECHNICAL FIELD

The present invention relates to an ultrasonic diagnostic apparatus for measuring the property of a tissue in an organism.

BACKGROUND ART

Recently, the number of people suffering from various circulatory system diseases, including heart infarction and brain infarction, has been on the rise, thus making it more and more urgent to prevent and treat these diseases.

The pathopoiesis of heart or brain infarction is closely correlated to arterial sclerosis. More specifically, if an atheroma is created on the arterial wall or if no arterial cells are produced anymore due to various factors such as elevated blood pressure, then the artery loses its elasticity to become hard and fragile. Also, if the blood vessel is clogged up where the atheroma has been created or if a vascular tissue covering the atheroma has ruptured, then the atheroma will move itself into the blood vessel to clog up the artery elsewhere or to rupture the hardened portions of the artery. As a result, these diseases are caused. That is why it is important to diagnose the arterial sclerosis as early as possible to prevent or treat these diseases.

In the prior art, the lesion of arterial sclerosis is diagnosed by directly observing the inside of the blood vessel with a vascular catheter. However, this diagnosis needs to be carried out with a vascular catheter inserted into the blood vessel of a subject, thus imposing a heavy load on him or her. A known method of diagnosing the arterial sclerosis easily without imposing excessively heavy load on a subject is measuring the index of cholesterol, which is one of major causes of arterial sclerosis, or the blood pressure. However, neither of these values directly indicates the degree of advancement of arterial sclerosis.

Also, if the arterial sclerosis can be diagnosed early enough to administer some medicine to its subject, then the disease can be treated effectively. However, it is said that once the arterial sclerosis has advanced to a certain degree, the farther advancement of that disease can be checked with the administration of medicine but it is difficult to repair the hardened artery completely.

That is why a method or apparatus for diagnosing the arterial sclerosis at an early stage of that disease (i.e., before the disease has advanced to a certain degree) without imposing too much load on a subject is now in high demand.

To meet such a demand, a diagnostic apparatus for diagnosing the arterial sclerosis at an early stage of that disease (i.e., before the disease has advanced too far) without imposing too much load on a subject has been proposed (see Patent Document No. 1, for example). An ultrasonic diagnostic apparatus is a noninvasive medical apparatus that imposes only a light load on a subject. The ultrasonic diagnostic apparatus is superior to an X-ray diagnostic apparatus, which is also a non-invasive medical apparatus, because the ultrasonic diagnosis can be made without administering a contrast medium to the subject or concerning about potential X-ray exposure. Specifically, by irradiating the subject with an ultrasonic wave that has been produced externally, the conventional ultrasonic diagnostic apparatus can acquire shape information or information about the variation in the shape of his or her internal body with time without causing pain to him or her. Thus, the vascular elastic property of the organism can be known and the degree of advancement of the arterial sclerosis can be detected directly.

The ultrasonic diagnostic apparatus disclosed in Patent Document No. 1 can track the object of measurement highly precisely by determining the instantaneous location of the subject by both the amplitude and phase of a detected output signal. According to this technique, vibration components can be measured precisely, and therefore, the thickness variation or strain of the vascular wall can be measured highly precisely on the order of several micrometers.

By adopting such a high-precision measuring technique, the two-dimensional distribution of the elastic property of the arterial wall can be plotted in detail. For example, Non-Patent Document No. 1 shows an example of presenting the two-dimensional distribution of the elastic property in color tones representing the degrees of elasticity by measuring the elastic property of the arterial vascular wall by the method of Patent Document No. 1.

Also, according to Non-Patent Document No. 1, after the elastic property of the iliac bone artery has been measured, the iliac bone is colored in vitro, thereby identifying the respective tissues of the iliac bone arterial wall. And by taking measurements based on the location information of the tissues that have been identified by coloring, it is determined which tissue each elastic property belongs to in the resultant two-dimensional distribution. Non-Patent Document No. 1 also teaches analyzing the defined elastic property of the tissue with a histogram and presuming the type of the tissue by reference to the two-dimensional distribution of the elastic property of the arterial wall, thereby defining the elastic property of each tissue.

Patent Document No. 1: Japanese Patent Application Laid-Open Publication No. 10-5226

Non-Patent Document No. 1: Hiroshi Kanai et al., "Elasticity Imaging of Atheroma with Transcutaneous Ultrasound Preliminary Study", Circulation, Vol. 107, pp. 3018-3021, 2003

DISCLOSURE OF INVENTION

Problems to be Solved by the Invention

As disclosed in Non-Patent Document No. 1, for example, by presenting the elastic property of each portion of the subject under measurement as a two-dimensional distribution, a unique portion of the elasticity of the subject can be detected easily. If the tissue in question or a predetermined region of the subject has various elastic property values, however, it cannot be seen easily what elastic property value the overall tissue or region has. In that case, it may be sometimes difficult to make an accurate pathologic diagnosis based on the elastic property of the subject.

In order to overcome the problems described above, an object of the present invention is to provide an ultrasonic diagnostic apparatus that can make a pathologic diagnosis of a subject more accurately based on his or her property measured value (such as the elastic property) that can be obtained by transmitting and receiving ultrasonic waves.

Means for Solving the Problems

An ultrasonic diagnostic apparatus according to the present invention includes: a transmitting section for driving a probe that transmits an ultrasonic wave toward a subject; a receiving section for amplifying a reflected echo to generate a received signal, the reflected echo being produced by getting the ultrasonic wave reflected by a vital tissue and received at the probe; an image processing section for generating a tomographic image of the subject based on the received signal; a region setting section for setting an arbitrary range of the tomographic image as a region of interest; a motion information gathering section for getting the motion information of the subject at multiple measuring points, which have been set on the subject based on the received signal; a property value calculating section for calculating the property measured values of multiple target tissues of the subject, specified by the multiple measuring points, by reference to the motion information; and a distribution plotting section, which gets the multiple property measured values and plots a frequency distribution of the property measured values based on the property measured values of the target tissues located within the region of interest that has been set by the region setting section.

In one preferred embodiment, the property measured values calculated by the property value calculating section are selected from the group consisting of the greatest thickness difference, strain and elastic property of the subject.

In another preferred embodiment, the region setting section sets the region of interest in response to a signal supplied from an external input section.

In still another preferred embodiment, the region setting section sets at least one boundary in the subject based on a characteristic of the received signal that is caused due to a difference in acoustic property in the subject. And the distribution plotting section plots the frequency distribution of the property measured values for each of the regions defined by the boundary.

In this particular preferred embodiment, the characteristic of the received signal is amplitude information of the received signal.

In yet another preferred embodiment, the region setting section sets at least one boundary in the subject based on the property measured values, and the distribution plotting section plots the frequency distribution of the property measured values for each of the regions defined by the boundary.

In yet another preferred embodiment, the region setting section sets at least one boundary in the subject based on the motion information, and the distribution plotting section plots the frequency distribution of the property measured values for each of the regions defined by the boundary.

In this particular preferred embodiment, the motion information is at least one of magnitudes of positional displacements of the subject with time between multiple measuring points and a variation in thickness with time between two points that define the target tissue.

In yet another preferred embodiment, the subject has a vascular wall tissue including an endosporium region, a media region and an adventitia region, and the region setting section sets at least one boundary between a vascular cavity and the endosporium region, between the endosporium region and the media region, between the media region and the adventitia region, and/or between the adventitia region and an extravascular tissue.

In yet another preferred embodiment, the distribution plotting section plots a histogram as the frequency distribution of the property measured values.

In yet another preferred embodiment, the ultrasonic diagnostic apparatus further includes a display for presenting the tomographic image and the frequency distribution thereon.

In yet another preferred embodiment, the image processing section gets the multiple property measured values and further generates an image representing a two-dimensional distribution of the property measured values in the subject.

In this particular preferred embodiment, the ultrasonic diagnostic apparatus further includes a display for presenting the tomographic image, the frequency distribution and the two-dimensional distribution image thereon.

In a specific preferred embodiment, the property value calculating section updates the property measured values at regular intervals, and the distribution plotting section and the image processing section update the frequency distribution and the two-dimensional distribution image, respectively, synchronously with the updates of the property measured values.

EFFECTS OF THE INVENTION

The ultrasonic diagnostic apparatus of the present invention can make and present the frequency distribution of property measured values of a subject within an arbitrary range based on the property of the subject in that range. As a result, the operator or a person who is inspecting the subject can easily know how high the elastic property of the region in question is. Also, if the operator specifies a region of interest for each constitutional tissue of the subject, he or she can refer to the frequency distributions of elastic properties on a constitutional tissue basis. Consequently, the subject can be inspected more accurately.

BRIEF DESCRIPTION OF DRAWINGS

FIG. 5($a$) is a graph showing an exemplary histogram that represents the elastic property of an adventitia region; FIG. 5($b$) is a graph showing an exemplary histogram that represents the elastic property of a media region; and FIG. 5($c$) is a graph showing an exemplary histogram that represents the elastic property of an endosporium region.

Figure 1:
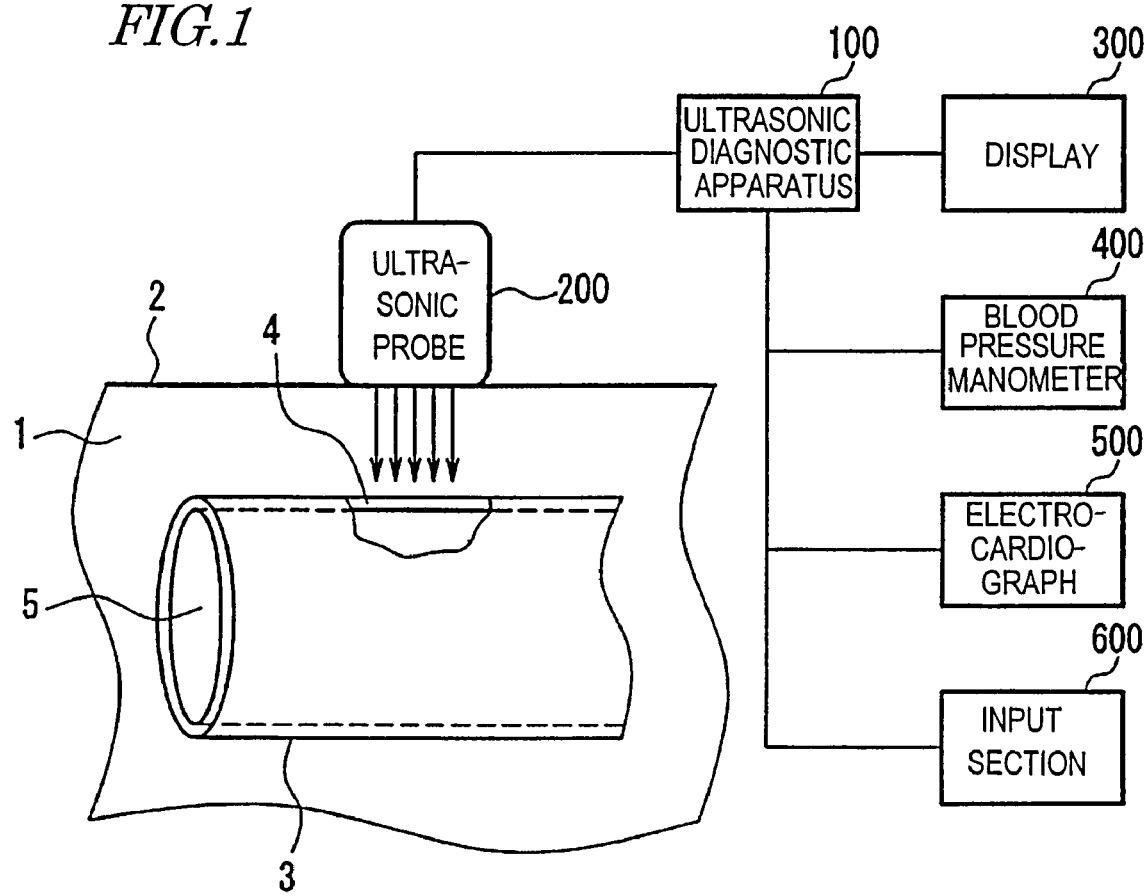
FIG. 1 shows an exemplary configuration for measuring the elastic property of a vascular wall using an ultrasonic diagnostic apparatus according to a first preferred embodiment of the present invention.

DESCRIPTION OF REFERENCE NUMERALS 1 internal vital tissue
2 body surface
3 blood vessel
4 vascular wall
5 blood
100 ultrasonic diagnostic apparatus
101 transmitting section
102 receiving section
103 time delay control section
104 motion information gathering section
105 property value calculating section
106 computed data storage section 107 region setting section
108 distribution plotting section
109 control section
110 image processing section
200 ultrasonic probe
300 display
400 blood pressure manometer
500 electrocardiograph
600 input section

BEST MODE FOR CARRYING OUT THE INVENTION

Hereinafter, preferred embodiments of an ultrasonic diagnostic apparatus according to the present invention will be described with reference to the accompanying drawings.

Embodiment 1

A first preferred embodiment will be described. In the following example, the elastic property of a vascular wall is measured with an ultrasonic diagnostic apparatus.

FIG. 1 shows an arrangement for measuring the elasticity of a vascular wall using the ultrasonic diagnostic apparatus of the first preferred embodiment. As shown in FIG. 1, the ultrasonic diagnostic apparatus 100 is connected to an ultrasonic probe 200, a display 300, a blood pressure manometer 400, an electrocardiograph 500 and an input section 600.

The ultrasonic probe 200 is a probe for transmitting and receiving an ultrasonic wave. As shown in FIG. 1, the ultrasonic probe 200 is held by the operator in close contact with the body surface 2 of a subject and transmits an ultrasonic wave toward a blood vessel 3. The ultrasonic wave is reflected by an internal vital tissue 1 and the vascular wall 4 and blood 5 of the blood vessel 3 to be a reflected echo, which eventually returns to the ultrasonic probe 200.

The ultrasonic diagnostic apparatus 100 receives the reflected echo with the ultrasonic probe 200 and analyzes the reflected echo, thereby presenting a tomographic image of the internal vital tissue 1 on the display 300, which may be a monitor, for example. The blood pressure manometer 400 is used to measure the blood pressure of the subject. And the electrocardiograph 500 is used to monitor the heartbeat of the subject.

The input section 600 is an input device such as a mouse, a keyboard or a touch screen panel. By operating the input section 600 by the method to be described later, the operator specifies a region of interest in the subject. The ultrasonic diagnostic apparatus 100 plots a frequency distribution of elasticities in the region of interest that has been specified and presents the frequency distribution on the display 300.

Figure 2:
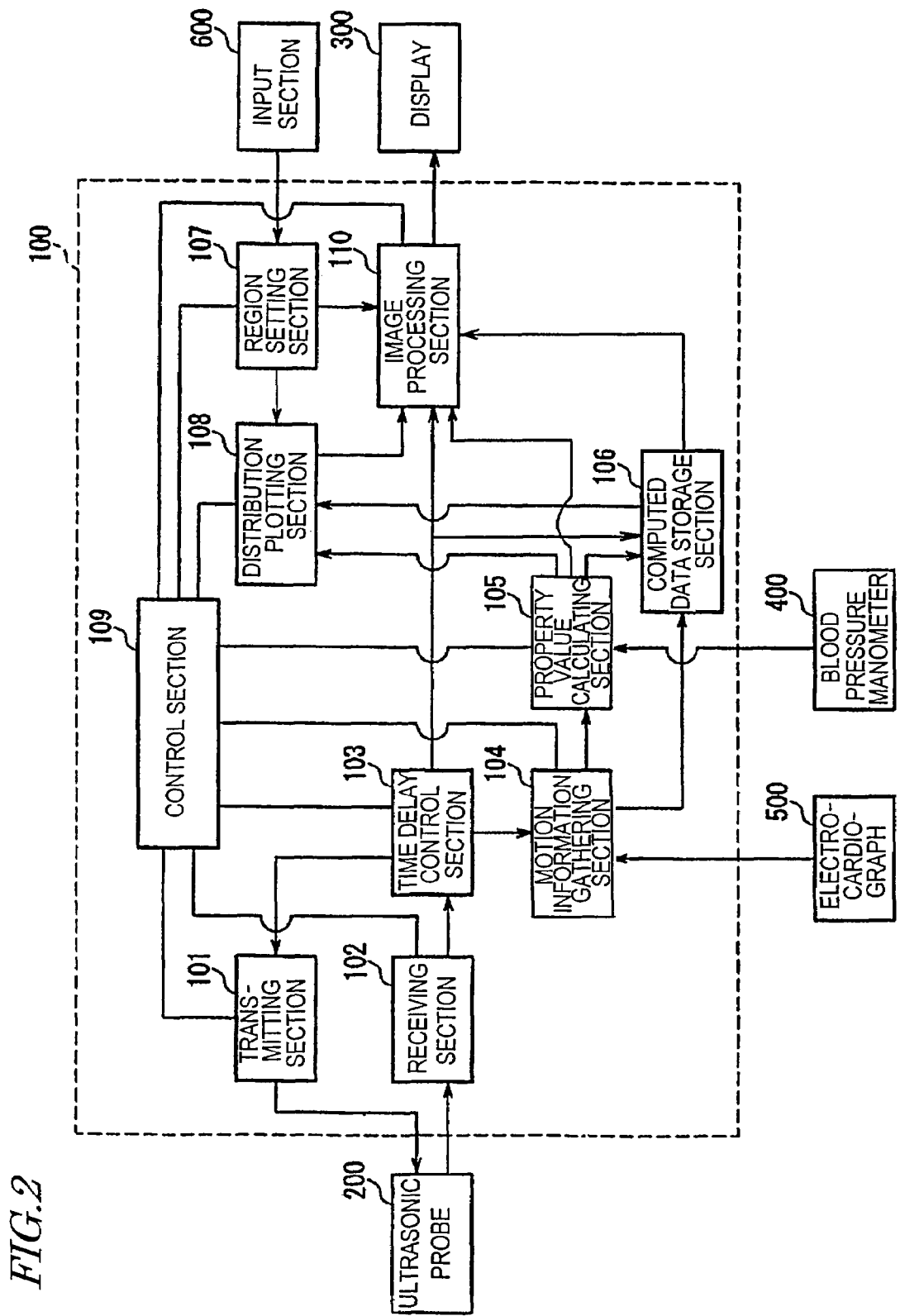
FIG. 2 is a block diagram showing a configuration for the ultrasonic diagnostic apparatus of the first preferred embodiment.

Next, the configuration of the ultrasonic diagnostic apparatus 100 will be described with reference to the accompanying drawings. FIG. 2 is a block diagram showing a configuration for the ultrasonic diagnostic apparatus 100. As shown in FIG. 2, the ultrasonic diagnostic apparatus 100 includes a transmitting section 101, a receiving section 102, a time delay control section 103, a motion information gathering section 104, an region setting section 107, a property value calculating section 105, a computed data storage section 106, a distribution plotting section 108, a control section 109 and an image processing section 110.

The control section 109 controls the transmitting section 101, the receiving section 102, the time delay control section 103, the motion information gathering section 104, the region setting section 107, the property value calculating section 105, the distribution plotting section 108 and the image processing section 110.

The transmitting section 101 transmits a predetermined drive pulse signal to the ultrasonic probe 200. On receiving the drive pulse signal, the ultrasonic probe 200 sends out an ultrasonic wave toward a subject. Also, the ultrasonic probe 200 receives an echo that has been reflected from the subject and converts the reflected echo into an electrical signal. The receiving section 102 receives the electrical signal from the ultrasonic probe 200 and amplifies it, thereby generating a received signal. Furthermore, the receiving section 102 gets the amplified received signal converted into a digital signal by an A/D converting section (not shown).

The time delay control section 103 instructs the transmitting section 101 to control the delay of the drive pulse signal to be transmitted to a group of piezoelectric elements in the ultrasonic probe 200. By controlling the time delay of the drive pulse signal, either the direction or the depth of focus of the ultrasonic wave to be sent out by the ultrasonic probe 200 is controlled (which is called "transmission focusing"). Also, the time delay control section 103 gets the received signal from the receiving section 102 and controls the delay of the received signal, thereby carrying out processing to get the received signal accurately from multiple directions (which is called "reception focusing") and outputting the received signal to the motion information gathering section 104 and the image processing section 110.

The motion information gathering section 104 gathers the motion information of the subject at multiple measuring points, which have been set on the subject, based on the received signal supplied from the time delay control section 103. More specifically, the motion information gathering section 104 figures out the magnitudes of positional displacements of the subject with time between the multiple measuring points that have been set on the subject and the temporal variations in the thicknesses of multiple target tissues of the subject that are defined by the multiple measuring points by the methods to be described later. These pieces of motion information that have been gathered here are output to the property value calculating section 105 and the computed data storage section 106. The motion information is output to both of the property value calculating section 105 and the computed data storage section 106 according to this preferred embodiment but may also be selectively output to either the property value calculating section 105 or the computed data storage section 106 only.

The property value calculating section 105 calculates the property measured values of the respective target tissues of the subject based on the motion information that has been obtained by the motion information gathering section 104. More specifically, the property value calculating section 105 calculates the greatest thickness difference and the strain between two points that define each of the target tissues by the method to be described later. Furthermore, the property value calculating section 105 also calculates the elastic property of each target tissue based on the blood pressure data collected by the blood pressure manometer 400 and the greatest thickness difference by the method to be described later. The property measured value is output to the computed data storage section 106 and the distribution plotting section 108. The property measured value is output to both of the computed data storage section 106 and the distribution plotting section 108 according to this preferred embodiment but may also be output selectively to either the computed data storage section 106 or the distribution plotting section 108 only.

The electrocardiogram obtained by the electrocardiograph 500 is output to the motion information gathering section 104 and the property value calculating section 105 and used as a trigger signal that determines the timings of data acquisition and data resetting. Any other trigger signal may also be used as long as the external device is connectible to the ultrasonic diagnostic apparatus 100 and generates a signal that can be used as a trigger signal. For example, the electrocardiogram obtained by the electrocardiograph 500 may be replaced with either a phonocardiogram obtained by a phonocardiograph or a sphygmogram obtained by a sphygmograph.

The region setting section 107 gets the region information of a region of interest (which will be abbreviated herein as "ROI") that has been specified by the operator using the input section 600. The region information contains information about the location and range of the ROI and defines a region of interest on a tomographic image of the subject as will be described in detail later. The distribution plotting section 108 plots a frequency distribution of property measured values in the ROI based on the region information obtained by the region setting section 107 and the property measured value calculated by the property value calculating section 105 by the method to be described later.

The image processing section 110 generates image data (such as a tomographic image) of the subject based on the received signal supplied from the time delay control section 103. Also, the image processing section 110 outputs the frequency distribution generated by the distribution plotting section 108, along with the tomographic image of the subject, to the display 300. Furthermore, the image processing section 110 outputs the region information, collected by the region setting section 107, to the display 300.

The computed data storage section 106 may be implemented as a semiconductor memory or a hard disk, for example, and stores the motion information gathered by the motion information gathering section 104 and the property measured value calculated by the property value calculating section 105. In accordance with the operator's instruction, the motion information and property measured value stored in the computed data storage section 106 are read out from the computed data storage section 106, processed by the image processing section 110 and then presented on the display 300. In this case, the property measured value is converted by the distribution plotting section 108 into a frequency distribution, which is then presented on the display 300. As a result, the operator can compare the data about the subject under test to the computed data that was collected in the past. The motion information and elastic property stored in the computed data storage section 106 do not have to be presented as frequency distributions but may also be represented in any other form.

Hereinafter, it will be described as an example exactly how the ultrasonic diagnostic apparatus 100 operates in a situation where the operator inspects the blood vessel 3 of a subject.

When the operator brings the ultrasonic probe 200 into contact with the body surface 2 of the subject, transmission focusing is done by the time delay control section 103 on the transmitting section 101, which transmits a drive pulse signal to the ultrasonic probe 200. In response, the ultrasonic probe 200 sends out an ultrasonic wave toward the internal vital tissue 1. The ultrasonic wave is reflected by the internal vital tissue 1, the vascular wall 4 and the blood 5 to be a reflected echo signal, which is eventually received by the ultrasonic probe 200.

The reflected echo received by the ultrasonic probe 200 is converted into an electrical signal, which is amplified, turned into a received signal and then converted into a digital signal by the receiving section 102. The received signal that has been converted digitally by the receiving section 102 is output to the time delay control section 103, which controls the delay of the received signal to carry out reception focusing and then outputs it to the motion information gathering section 104 and image processing section 110.

The motion information gathering section 104 obtains motion information such as a thickness variation from the received signal by the method to be described later. According to this preferred embodiment, a phase detection method, which is qualified for obtaining motion information with a high resolution, is adopted as a method for gathering the motion information. However, the motion information does not have to be collected by this method but may also be obtained by an envelope detection method, for example.

The motion information gathering section 104 detects the phase of the received signal, supplied from the time delay control section 103, thereby splitting the signal into a real part signal and an imaginary part signal, which are then subjected to filtering processing to filter out the components that have not been reflected by the object of measurement and other noise components.

Figure 7:
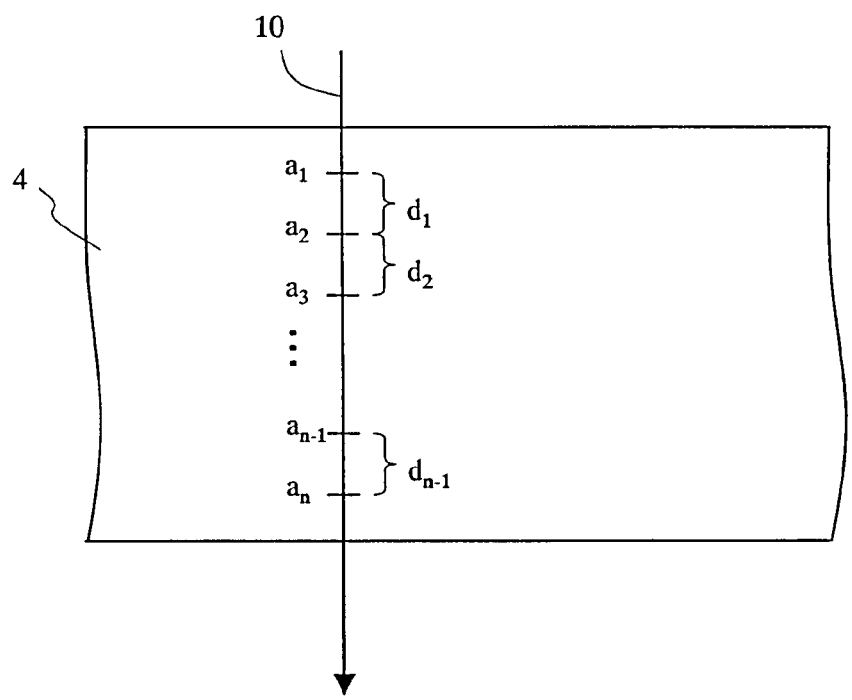
FIG. 7 shows measuring points that are set on a vascular wall.

FIG. 7 schematically shows the acoustic line 10 of the ultrasonic wave that has been transmitted from the ultrasonic probe 200 and is propagating through the vascular wall 4 of the subject. As shown in FIG. 7, multiple measuring points $a_1$, $a_2$, $a_3$, . . . , and $a_n$ are set at regular intervals on the acoustic line 10. Also, the target tissues $d_1$, $d_2$, . . . , and $d_{n-1}$ of the vascular wall 4 are defined by respective pairs of adjacent measuring points $a_1$ and $a_2$, $a_2$ and $a_3$, . . . , and $a_{n-1}$ and $a_n$. Only one acoustic line 10 is shown in FIG. 7. However, as the ultrasonic probe 200 scans the vascular wall 4 in its length direction (i.e., the direction in which the blood vessel extends), there will be a number of parallel acoustic lines 10 at regular intervals in an actual measurement. As a result, the measuring points are arranged two-dimensionally in the subject and the target tissues defined by the measuring points in the subject are also arranged two-dimensionally. A target tissue is normally defined by two adjacent measuring points. Alternatively, a target tissue may also be defined by measuring points that are spaced apart from each other by a distance of two or more (e.g., the measuring points $a_1$ and $a_3$).

Using the real part signal and imaginary part signal, the motion information gathering section 104 calculates the motion velocities of the subject at the respective measuring points by a restricted minimum square method, for example. Then, the motion information gathering section 104 integrates the motion velocities with respect to time, thereby calculating the magnitudes of positional displacements of the subject with time between the respective measuring points. Also, the motion information gathering section 104 calculates the difference between the magnitudes of positional displacements with time at two adjacent measuring points on the same acoustic line, thereby figuring out the variation in the thickness of each target tissue. If the target tissue is defined by a pair of measuring points that are spaced apart from each other by a distance of two or more as described above, then the motion information gathering section 104 calculates the difference between the magnitudes of positional displacements with time at the two measuring points that define the position of the target tissue.

For example, the respective measuring points may be set at an interval of 80 μm and the variation in the thickness of the target tissue, defined at the 80 μm interval, may be calculated. Alternatively, the target tissues may also be defined at an interval of 160 μm or 240 μm. In this case, the thickness variation does not have to be calculated by the method described above but may be calculated by any other method as long as a variation in thickness between two arbitrary points can be calculated.

The property value calculating section 105 calculates the greatest thickness difference as a difference between the maximum and minimum variations in the thicknesses of multiple target tissues, which have been calculated by the motion information gathering section 104 during an arbitrary period, and also figures out a strain between the two points based on the greatest thickness difference. Supposing the greatest thickness difference is Δh and the maximum thickness of the subject is H, the strain S may be given by the following Equation (1):

$$S=\Delta h/H \quad (1)$$

Furthermore, based on the blood pressure data provided by the blood pressure manometer 400 and the magnitude of the strain calculated by Equation (1), the property value calculating section 105 figures out an elastic property between the two points. Supposing the difference between the maximum and minimum values of the blood pressures (i.e., the pulse pressure) acquired from the blood pressure manometer 400 in the periods during which the maximum and minimum thickness variations are obtained is Δp, the elastic property E may be given by the following Equation (2):

$$E=\Delta p/S=\Delta p \cdot H/\Delta h \quad (2)$$

If the subject is a circulatory organ such as the vascular wall 4, then the greatest thickness difference Δh, the pulse pressure Δp and the maximum thickness H change one cardiac cycle after another. That is why the maximum and minimum values of the thickness variations of the target tissues are preferably obtained every cardiac cycle. In that case, the greatest thickness difference Δh and strain S are also calculated every cardiac cycle. The elastic property E is also figured out once a cardiac cycle using the maximum and minimum blood pressure values that are obtained every cardiac cycle. That is to say, an property measured value such as the elastic property E is updated one cardiac cycle after another.

The image processing section 110 generates image data representing a tomographic image of the blood vessel 3 based on the received signal obtained by the time delay control section 103 and outputs the image data to the display 300. It should be noted that the data does not have to be presented on the display 300 as in the following example.

Figure 3:
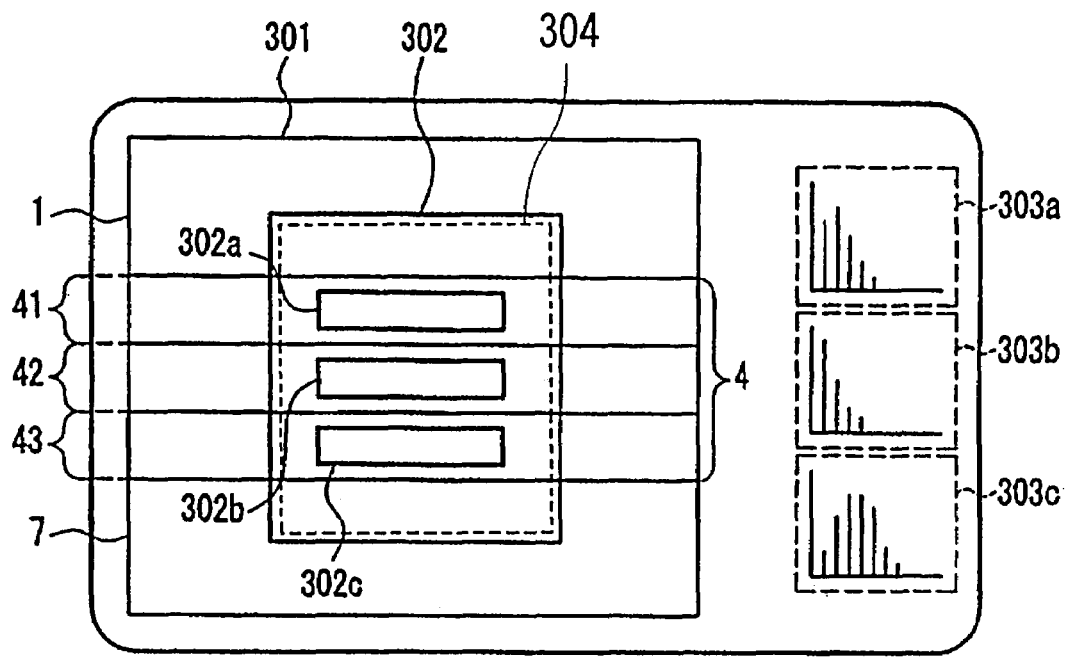
FIG. 3 illustrates an exemplary picture presented on the display by the ultrasonic diagnostic apparatus shown in FIG. 2.

FIG. 3 illustrates an exemplary mode of presentation on the display 300. As shown in FIG. 3, the picture presented on the display 300 includes a tomographic image display area 301, an elastic property ROI 302, and histogram display areas 303a, 303b and 303c.

In the tomographic image display area 301, tomographic images of the subject, which have been generated based on the image data supplied from the image processing section 110, are presented. In this preferred embodiment, the vascular wall 4 of the blood vessel 3 as a subject is presented in B mode in the tomographic image display area 301. The vascular wall 4 includes an adventitia 41, a media 42 and an endosporium 43. It should be noted that the adventitia 41, the media 42 and the endosporium 43 are illustrated in FIG. 3 schematically, not to scale.

The elastic property ROI 302 is an ROI, of which the size (or range) and the location may be specified arbitrarily by the operator. The motion information gathering section 104 and property value calculating section 105 calculate the greatest thickness difference, the strain, the elastic property and other property measured values of the subject's target tissues at least in the range that has been set in the elastic property ROI 302. As described above, the target tissues are arranged two-dimensionally and the elastic property ROI 302 includes a two-dimensional arrangement of target tissues. The elastic property ROI 302 representing the size and location that have been set is presented in real time in the tomographic image display area 301. For example, the size and location of the elastic property ROI 302 may be defined so as to cover the vascular wall 4 both vertically and horizontally as shown in FIG. 3.

The elastic property ROI 302 includes histogram ROIs 302a, 302b and 302c, of which the number, the sizes (ranges) and locations may be specified arbitrarily by the operator. The histogram ROIs 302a, 302b and 302c are ranges in which histograms should be plotted. The histogram ROIs 302a, 302b and 302c in the arbitrarily specified sizes, locations and numbers are presented in real time in the tomographic image display area 301. For example, the sizes, locations and number of the histogram ROIs 302a, 302b and 302c may be defined so as to respectively represent the adventitia 41, media 42 and endosporium 43 of the vascular wall 4 as shown in FIG. 3. Each of these histogram ROIs 302a, 302b and 302c includes a two-dimensional arrangement of target tissues.

Hereinafter, it will be described how the operator may specify the elastic property ROI 302 and histogram ROIs 302a, 302b and 302c in the tomographic image representing the vascular wall 4 of the blood vessel 3 in the tomographic image display area 301.

The sizes and number of the ROIs in the elastic property ROI 302 may be defined by letting the operator determine the vertical and horizontal sizes (i.e., the height and the width) and the number of the ROIs with the input section 600 (which may be a control panel, for example). To allow him or her to determine the sizes easily, several combinations of sample heights, widths and numbers may be prepared in advance for the input section 600. By selecting desired values from those sample values, the operator can specify the elastic property ROI 302. The location of the elastic property ROI 302 may be determined by letting the operator specify his or her desired location with the input section 600 (which may be a trackball, for example).

The elastic property ROI 302 may be set not only by using a control panel and a trackball as the input section 600 as in the histogram ROIs 302a, 302b and 302c but also by operating the input section 600 (which may be a pointing device such as a mouse) in the following manner.

For example, the operator may handle the mouse such that a mouse pointer (not shown) on the tomographic image display area 301 points to an arbitrary point (which will be referred to herein as a "start point"). When the operator clicks the left button of the mouse at the start point (with coordinates (X1, Y1)) pointed to by the mouse pointer, the location of the start point is fixed.

To define his or her desired ROI, the operator further makes a drag operation with the mouse, thereby moving the mouse pointer to another arbitrary point (which will be referred to herein as an "end point"). When the operator lifts his or her finger from the mouse button at the end point (with coordinates (X2, Y2)) pointed to by the mouse pointer, the location of the end point is fixed. Values representing either the location (e.g., the information about the coordinates on the display 300) of a rectangular area, of which the diagonal is defined by the line segment connecting the start and end points together, or its range (i.e., the vertical and horizontal lengths of the rectangular area) are used as pieces of region information.

The ROIs are set at least twice when the region for measuring the thickness variation, the strain or the elastic property (i.e., the elastic property ROI 302) is defined and when regions for plotting the histograms (i.e., the histogram ROIs 302a, 302b and 302c) are defined.

The region information of the elastic property ROI 302 and that of the histogram ROIs 302a, 302b and 302c are output as measuring region information and histogram region information, respectively, to the ROI setting section 107. It should be noted that the ROIs do not always have to be defined as described above according to this preferred embodiment. For example, if the input section 600 is a keyboard, the ROIs may also be defined by letting the operator enter the coordinates directly with the keyboard.

Next, it will be described how to plot histograms based on the measuring region information and the histogram region information that have been defined for the region setting section 107.

The distribution plotting section 108 gets the property measured value such as the thickness variation, strain or elastic property of the target tissue, included in the range defined by the measuring region information in the region setting section 107, from the property value calculating section 105. Also, the distribution plotting section 108 plots the frequency distributions of the elastic properties of multiple target tissues, included in the range defined by the histogram region information in the region setting section 107, thereby making histograms. Every time the property value calculating section 105 updates the property measured value, the distribution plotting section 108 preferably plots the frequency distribution and makes new histograms all over again at the same intervals as the update.

For example, the distribution plotting section 108 may plot the frequency distribution of elastic properties and make histograms by counting the frequencies of elastic properties on an elastic property level (of 100 mmHg, for instance) basis. The histograms are output by the image processing section 110 to the display 300. In the histogram display area 303a, presented is a histogram representing the elastic property of a target tissue included in some region of the adventitia 41, which has been defined in the histogram ROI 302a. In the same way, histograms representing the elastic properties of respective target tissues included in some region of the media 42 and in some region of the endosporium 43, which have been defined in the histogram ROIs 302b and 302c, are presented in the histogram display areas 303b and 303c, respectively.

As soon as the motion information gathering section 104 and the property value calculating section 105 get calculations done, the distribution plotting section 108 makes histograms in the ranges defined by the measuring region information. Thus, no sooner have the measurements been done than the respective histograms are presented in the histogram display areas 303a, 303b and 303c of the display 300.

FIG. 5 shows histograms that were made based on results obtained by measuring the elastic property of the carotid arterial vascular wall of a 36 years old healthy man. Specifically, FIG. 5(a) is a graph showing an exemplary histogram that represents the elastic property of an adventitia region; FIG. 5(b) is a graph showing an exemplary histogram that represents the elastic property of a media region; and FIG. 5(c) is a graph showing an exemplary histogram that represents the elastic property of an endosporium region. In FIGS. 5(a) through 5(c), the abscissa represents the elastic property (in mmHg) and the ordinate represents the frequency within the region.

The histogram shown in FIG. 5(a) is obtained by plotting the frequency distribution of the elastic properties of target tissues included in the histogram ROI 302a shown in FIG. 3. In the histogram ROI 302a, 12 target tissues are arranged in the vascular wall thickness direction, 50 target tissues are arranged in the direction in which the blood vessel extends, and 500 target tissues are included in total. In the same way, the histogram shown in FIG. 5(b) is obtained based on the elastic properties of target tissues included in the histogram ROI 302b. In the histogram ROI 302b, 6 target tissues are arranged in the vascular wall thickness direction, 50 target tissues are arranged in the direction in which the blood vessel extends, and 300 target tissues are included in total. The histogram shown in FIG. 5(c) is obtained based on the elastic properties of target tissues included in the histogram ROI 302c. In the histogram ROI 302c, 3 target tissues are arranged in the vascular wall thickness direction, 50 target tissues are arranged in the direction in which the blood vessel extends, and 150 target tissues are included in total. As mentioned above, the adventitia 41, media 42 and endosporium 43 are not illustrated to scale in FIG. 3, and therefore, the histogram ROIs 302a, 302b and 302c are also shown schematically there.

FIG. 5(a) shows that the frequencies of elastic properties of 150 mmHg to 550 mmHg are high, which indicates that most of the tissues in the adventitia region defined by the histogram ROI 302a have elastic properties falling within this range. FIG. 5(b) shows that most of the tissues in the media region defined by the histogram ROI 302b have elastic properties falling within the range of 150 mmHg to 250 mmHg.

FIG. 5(c) shows that most of the tissues in the endosporium region have elastic properties falling within the range of 50 mmHg to 750 mmHg. It can also be seen that there are tissues with elastic properties of 1,000 mmHg or more. These high elastic properties are isolated from the main elastic property distribution within the range of 50 mmHg to 750 mmHg. Thus, it can be seen that there are some tissues with outstandingly high elastic properties within the region defined by the endosporium histogram ROI 302c.

Figure 6:
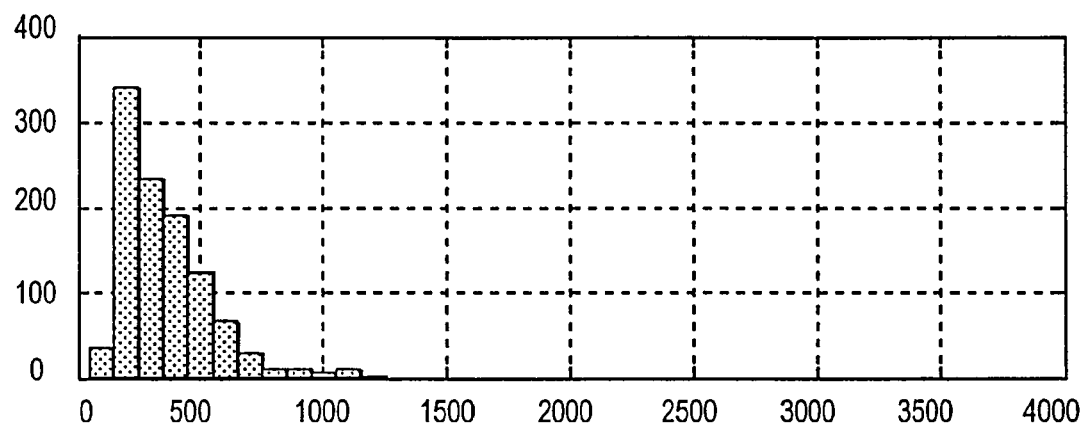
FIG. 6 is a graph showing an exemplary elastic property histogram of the entire vascular wall including the endosporium, media and adventitia regions.

For the purpose of comparison, FIG. 6 shows an exemplary histogram made by defining a single histogram ROI, covering the histogram ROIs 302a, 302b and 302c, using the ultrasonic diagnostic apparatus 100 and plotting the frequency distribution of elastic properties of target tissues included in the region defined. The histogram ROI defined includes the adventitia, media and endosporium of the vascular wall. The histogram shown in FIG. 6 indicates that there are some tissues with elastic properties of more than 1,000 mmHg. According to the distribution of elastic properties, however, it is difficult to determine whether the presence of tissues with such high elastic properties is exceptional or not.

As can be seen, the adventitia, media and endosporium regions have different elastic property histograms. That is why in measuring the elastic property of a vascular wall and determining the degree of advancement of sclerosis, it would be very effective to make histograms on a constitutional tissue basis in order to make an accurate pathologic diagnosis.

It should be noted that the number of histograms made for each histogram ROI does not have to be one. For example, if the operator has specified only the histogram ROI 302a, the distribution plotting section 108 may measure the elastic properties, thickness variations and strains in the histogram ROI 302a, make three histograms representing the elastic properties, thickness variations and strains, respectively, and present those histograms in the histogram display areas 303a, 303b and 303c.

As described above, according to this preferred embodiment, the region setting section 107 gets the region information of the ROI that has been specified by the operator and the distribution plotting section 108 makes a histogram representing the frequencies of elastic properties in the defined ROI based on the region information and the elastic properties measured by the property value calculating section 105. In this manner, the frequency distribution of elastic properties in the region defined in the subject is shown. As a result, the operator or a person who is inspecting the subject can easily know how high the elastic property of the region in question is. Also, if the operator specifies an ROI for each constitutional tissue of the subject, he or she can refer to histograms representing the elastic properties of the constitutional tissues. Thus, the operator can understand the exact degree of advancement of sclerosis in the subject by reference to the elastic properties of respective constitutional tissues of the subject, and can make an even more accurate pathologic diagnosis. Furthermore, in the ultrasonic diagnostic apparatus of this preferred embodiment, the property value calculating section 105 obtains computed data and the distribution plotting section 108 makes histograms based on the computed data. As a result, the operator can understand the degree of advancement of sclerosis in the subject immediately, and can make an even more accurate diagnosis.

In the preferred embodiment described above, the vascular wall 4 is supposed to be made up of the adventitia 41, media 42 and endosporium 43, for which histograms are made separately. However, as the endosporium and media are often used as an intima-media complex (IMC) region, the vascular wall 4 may also be supposed to include the adventitia 41 and the IMC region and histograms may be made for these two regions.

Also, in the preferred embodiment described above, the property measured values calculated by the property value calculating section 105 are presented only as a frequency distribution such as a histogram. Alternatively, a two-dimensional distribution image, representing the property measured values as locations in the subject, may be further generated and presented. For example, if the operator has specified the elastic property ROI 302 as shown in FIG. 3, the image processing section 110 may generate a two-dimensional distribution image representing the elastic properties of target tissues included in the elastic property ROI 302 based on the elastic property values supplied from the property value calculating section 105 and the region information of the elastic property ROI 302 provided by the region setting section 107. Then, the image processing section 110 may get a two-dimensional distribution image 304 of the elastic properties superimposed on the tomographic image display area 301 on the display 300. Since the elastic property value is updated every cardiac cycle as described above, the image processing section 110 also preferably updates the two-dimensional distribution image every cardiac cycle synchronously with the update of the elastic property. As a result, the elastic property histogram and the two-dimensional distribution image are updated synchronously with each other every cardiac cycle.

Optionally, in that case, the elastic property ROI 302 may be aligned with the histogram ROI such that if the elastic property ROI 302 is selected, the histogram ROI is also defined automatically. By adopting such a technique, even if the operator does not specify a region in which the frequency distribution of elastic properties needs to be obtained, a two-dimensional distribution image representing elastic properties and their histogram can also be presented.

As described above, if a two-dimensional distribution image representing elastic properties is also presented, a specific portion of the subject's elastic property can be detected easily by reference to the two-dimensional distribution image of the elastic properties. In addition, as described above, it can also be determined easily, by reference to the elastic property histogram, how much the elastic properties are varied and whether or not the elastic property value in question is a specific value on the frequency distribution of elastic properties. Consequently, the operator can make an even more accurate pathologic diagnosis based on these pieces of information.

Embodiment 2

Hereinafter, a second preferred embodiment of the present invention will be described with reference to the accompanying drawings. The ultrasonic diagnostic apparatus of the second preferred embodiment is the same as the counterpart of the first preferred embodiment described above except how the region setting section 107 sets the ROI.

Figure 4:
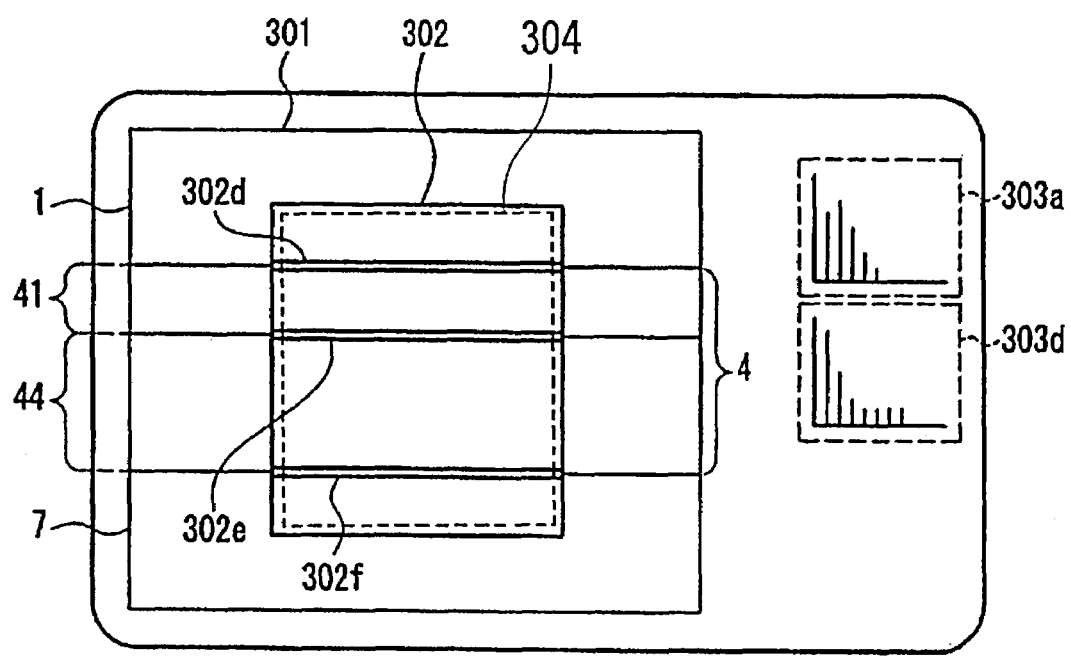
FIG. 4 illustrates an exemplary picture presented on the display by an ultrasonic diagnostic apparatus according to a second preferred embodiment of the present invention.

FIG. 4 illustrates an exemplary picture presented on the display of the ultrasonic diagnostic apparatus of this preferred embodiment. In FIG. 4, any component of the display 300, having the same function as the counterpart of the first preferred embodiment described above, is identified by the same reference numeral as that used in FIG. 3 and the description thereof will be omitted herein.

As shown in FIG. 4, the ultrasonic diagnostic apparatus of this preferred embodiment gets a tomographic image display area 301, an elastic property ROI 302, and histogram display areas 303a, 303d presented on the display 300.

In the tomographic image display area 301, a picture of the vascular wall 4 of the blood vessel 3 as a subject may be presented as a B-mode image, for example. The vascular wall 4 is made up of an adventitia 41 and an IMC region 44 including a media and an endosporium.

According to this preferred embodiment, the operator can specify an ROI by setting a boundary in the elastic property ROI 302 presented on the display 300. If one or more boundaries are set, the elastic property ROI 302 is divided into two or more regions to be histogram ROIs, for which histograms should be made separately. A histogram ROI may be defined as a region interposed between two boundaries.

In the example illustrated in FIG. 4, the region interposed between the boundaries 302d and 302e (i.e., a portion of the adventitia 41 of the vascular wall 4) is specified as a ROI and the region interposed between the boundaries 302e and 302f (i.e., a portion of the IMC region 44 of the vascular wall 4) is specified as another ROI.

The ROIs defined by the boundaries 302d, 302e and 302f are presented in real time in the tomographic image display area 301. The sizes, locations and number of the ROIs are determined by the boundaries 302d, 302e and 302f and the elastic property ROI 302. That is why these pieces of information of the ROIs need not be presented on the display 300.

Hereinafter, it will be described how the operator specifies ROIs using the boundaries 302d, 302e and 302f on the tomographic image of the vascular wall 4 of the blood vessel 3 that is presented on the tomographic image display area 301.

The operator sets the boundary 302d by operating the input section 600 (e.g., a pointing device such as a mouse). For example, the operator may handle the mouse such that the mouse pointer on the tomographic image display area 301 points to an arbitrary point (which will be referred to herein as a "Point A"). When the operator clicks the mouse at Point A pointed to by the mouse pointer, the boundary 302d, of which the length is substantially equal to the horizontal length of the elastic property ROI 302, is presented.

By repeatedly performing this operation, the other boundaries 302e and 302f are also set in the same way. Optionally, the operator may also move the boundaries 302d, 302e and 302f by dragging them, for example.

Values representing the location of each region interposed between two boundaries (such as coordinate information on the display 300) and values representing the range of that region (i.e., the horizontal and vertical lengths of a rectangular region) are used as pieces of region information. The region information defined by the boundaries 302d, 302e and 302f is output as histogram region information to the region setting section 107.

However, the ROI does not have to be defined in this manner. For example, if the input section 600 is a keyboard, the operator may specify the ROI by directly entering coordinates with the keyboard. Alternatively, using a pointing device such as a mouse as the input section 600, the operator may manipulate the mouse freely while viewing the pointer on the tomographic image display area 301 and may use the mouse's trace as a boundary. Then, even complex boundaries can also be set relatively easily.

Still alternatively, the boundaries may be set by the ultrasonic diagnostic apparatus automatically. The tissues included in the subject have mutually different acoustic properties. That is why the received signals, generated by receiving reflected echoes, have different characteristics that are caused due to the difference in acoustic property. More specifically, the intensities (i.e., amplitude information) of the received signals reflect the various acoustic properties of the respective tissues. For that reason, the boundary may be set automatically in accordance with the amplitude information of the received signal. In this preferred embodiment, the image processing section 110 generates image data such as a subject's tomographic image based on the received signal. This image data is generated by getting the amplitude of the received signal amplified by a log amplifier. And the intensities of the received signals may be characterized on a tissue-by-tissue basis or on a boundary between different tissues. Consequently, by receiving the image data such as a tomographic image that has been generated by the image processing section 110, the region setting section 107 can set the boundaries based on the difference in the amplitude of the image data.

Also, the difference in property measured value such as the greatest thickness difference, strain or elastic property may be sensed as a subject's boundary. Just like the amplitude of the received signal, the property measured value is also specific to each tissue. That is why the region setting section 107 may detect the boundary between tissues automatically by sensing the difference in the greatest thickness difference, strain or elastic property.

Furthermore, the difference in motion information such as the magnitude of positional displacement or the thickness variation of the subject may also be sensed as a subject's boundary. The motion information is also specific to each tissue. That is why the region setting section 107 may detect the boundary between tissues automatically by sensing the difference in the greatest thickness difference, strain or elastic property.

In the preferred embodiments described above, the subject is supposed to be the arterial vascular wall. However, the subject that can be measured with the ultrasonic diagnostic apparatus of the present invention does not have to be the blood vessel. Alternatively, the ultrasonic diagnostic apparatus of the present invention can also be used effectively to measure and inspect the heart, liver, stomach or any other tissue and make a pathologic diagnosis based on an property measured value such as elastic property as described above.

Also, in any of the preferred embodiments of the present invention described above, if it is difficult for the operator to specify an ROI while operating the ultrasonic probe 200, then the apparatus may go offline once using a freeze function and then present an intra-ROI histogram after the ROI has been specified.

Furthermore, in the preferred embodiments described above, the regions where histograms should be made (e.g., the histogram ROIs 302a, 302b and 302c) are supposed to be defined on the elastic property ROI 302. However, it is not always necessary to set the elastic property ROI 302. For example, if the ultrasonic diagnostic apparatus has such high processability as to figure out the elastic property over the entire screen, those regions where histograms should be made may be directly defined on the tomographic image display area 301.

INDUSTRIAL APPLICABILITY

The ultrasonic diagnostic apparatus of the present invention can be used effectively to measure a subject's property measured value such as the elastic property and make a pathologic diagnosis or analyze the property of a tissue included in the subject.

The invention claimed is:

1. An ultrasonic diagnostic apparatus comprising:
   a transmitting section for driving a probe that transmits an ultrasonic wave toward a subject;
   a receiving section for amplifying a reflected echo to generate a received signal, the reflected echo being produced by getting the ultrasonic wave reflected by a vital tissue and received at the probe;
   an image processing section for generating a tomographic image of the subject based on the received signal;
   a region setting section for setting an arbitrary range of the tomographic image as a region of interest;
   a motion information gathering section for getting the motion information of the subject at multiple measuring points, which have been set on the subject, based on the received signal;
   a property value calculating section for calculating the property measured values of multiple target tissues of the subject, specified by the multiple measuring points, by reference to the motion information; and
   a distribution plotting section, which gets the multiple property measured values and plots a frequency distribution of the property measured values based on the property measured values of the target tissues located within the region of interest that has been set by the region setting section;
   wherein the region setting section sets at least one boundary in the subject based on a characteristic of the received signal that is caused due to a difference in acoustic property in the subject, and
   wherein the distribution plotting section plots the frequency distribution of the property measured values for each of the regions defined by the boundary.

2. The ultrasonic diagnostic apparatus of claim 1, wherein the property measured values calculated by the property value calculating section are selected from the group consisting of the greatest thickness difference, strain and elastic property of the subject.

3. The ultrasonic diagnostic apparatus of claim 1, wherein the region setting section sets the region of interest in response to a signal supplied from an external input section.

4. The ultrasonic diagnostic apparatus of claim 1, wherein the characteristic of the received signal is amplitude information of the received signal.

5. The ultrasonic diagnostic apparatus of claim 1, wherein the region setting section sets at least one boundary in the subject based on the property measured values, and
  wherein the distribution plotting section plots the frequency distribution of the property measured values for each of the regions defined by the boundary.

6. The ultrasonic diagnostic apparatus of claim 1, wherein the region setting section sets at least one boundary in the subject based on the motion information, and
  wherein the distribution plotting section plots the frequency distribution of the property measured values for each of the regions defined by the boundary.

7. The ultrasonic diagnostic apparatus of claim 6, wherein the motion information is at least one of magnitudes of positional displacements of the subject with time between multiple measuring points and a variation in thickness with time between two points that define the target tissue.

8. The ultrasonic diagnostic apparatus of claim 1, wherein the subject has a vascular wall tissue including an endosporium region, a media region and an adventitia region, and
  wherein the region setting section sets at least one boundary between a vascular cavity and the endosporium region, between the endosporium region and the media region, between the media region and the adventitia region, and/or between the adventitia region and an extravascular tissue.

9. The ultrasonic diagnostic apparatus of claim 1, wherein the distribution plotting section plots a histogram as the frequency distribution of the property measured values.

10. The ultrasonic diagnostic apparatus of claim 1, further comprising a display for presenting the tomographic image and the frequency distribution thereon.

11. The ultrasonic diagnostic apparatus of claim 1, wherein the image processing section gets the multiple property measured values and further generates an image representing a two-dimensional distribution of the property measured values in the subject.

12. The ultrasonic diagnostic apparatus of claim 11, further comprising a display for presenting the tomographic image, the frequency distribution and the two-dimensional distribution image thereon.

13. The ultrasonic diagnostic apparatus of claim 12, wherein the property value calculating section updates the property measured values at regular intervals, and wherein the distribution plotting section and the image processing section update the frequency distribution and the two-dimensional distribution image, respectively, synchronously with the updates of the property measured values.

* * * * *